United States Patent
Heuser et al.

(10) Patent No.: US 6,554,842 B2
(45) Date of Patent: Apr. 29, 2003

(54) SMALL DIAMETER SNARE

(75) Inventors: Richard R. Heuser, Phoenix, AZ (US); Richard M. DeMello, Acton, MA (US)

(73) Assignee: Radius Medical Technologies, Inc., Acton, MA (US)

(*) Notice: Subject to any disclaimer, the term of this patent is extended or adjusted under 35 U.S.C. 154(b) by 0 days.

(21) Appl. No.: 09/803,308

(22) Filed: Mar. 9, 2001

(65) Prior Publication Data

US 2001/0031970 A1 Oct. 18, 2001

Related U.S. Application Data

(60) Provisional application No. 60/188,390, filed on Mar. 10, 2000.

(51) Int. Cl.[7] .............................................. A61F 11/00
(52) U.S. Cl. ....................................... 606/108; 606/113
(58) Field of Search ................................. 606/113, 127, 606/114, 200, 159, 108

(56) References Cited

U.S. PATENT DOCUMENTS

| | | | | |
|---|---|---|---|---|
| 5,123,906 A | * | 6/1992 | Kelman | 606/107 |
| 5,376,094 A | * | 12/1994 | Kline | 606/113 |
| 5,387,219 A | | 2/1995 | Rappe | |
| 5,522,819 A | | 6/1996 | Graves et al. | |
| 5,697,936 A | * | 12/1997 | Shipko et al. | 606/108 |
| 5,868,754 A | * | 2/1999 | Levine et al. | 606/108 |
| 6,338,727 B1 | * | 1/2002 | Noda et al. | 604/113 |
| 6,379,319 B1 | * | 4/2002 | Garibotto et al. | 600/585 |

FOREIGN PATENT DOCUMENTS

| | | |
|---|---|---|
| DE | 9412370 U1 | 12/1995 |
| WO | WO 99/44524 | 9/1999 |
| WO | WO 99/51149 | 10/1999 |

\* cited by examiner

Primary Examiner—John J. Calvert
Assistant Examiner—Alissa L. Hoey
(74) Attorney, Agent, or Firm—Cesari and McKenna, LLP

(57) ABSTRACT

A small-diameter surgical snare device that is capable of fitting through existing balloon or guiding catheters includes metal tubing along a section of a core wire. The distal end of the core wire connects to one or more snare wires that form the snaring loop. The distal end of the snaring loop supports a radiopaque coil or collar that makes the end of the loop visible under fluoroscopy. The snaring loop may consist of one or two wires or an overlap of a tapered end of the core wire. A radiopaque coil is attached to a distal end of the metal tubing, to provide flexibility and visibility to a distal region of the device. Alternatively, a polyimide tube and a short radiopaque marker may be included at a distal end of the metal tubing. The polyimide tube fits inside of the metal tubing, to add strength and torsion control to the distal region of the device, while the radiopaque marker adds visibility. In all embodiments, a shrink tube is fit over the radiopaque coil or marker that is supported by the distal end of the metal tubing, to ensure that the coil does not stretch when the snaring loop is extended during use.

30 Claims, 7 Drawing Sheets

SMALL DIAMETER SNARE

CROSS-REFERENCE TO RELATED APPLICATIONS

This application claims priority from U.S. Provisional Patent Application Ser. No. 60/188,390 entitled SMALL DIAMETER SNARE filed Mar. 10, 2000.

BACKGROUND OF THE INVENTION

1. Field of the Invention

The present invention relates to surgical snares and more particularly to devices for retrieving broken, dislodged, or separated medical devices from within the vascular system.

2. Background Information

Certain snare devices have become available over recent years for retrieving malfunctioning or misplaced devices within the cardiovascular and non-vascular regions of the body. These typically consist of fairly large diameter sheaths, which house a movable central wire or wires whose distal ends are formed into a loop or loops. The loop is used to ensnare and capture the desired object for withdrawal and removal from the body. In use, the snare is typically passed through a guiding catheter or other introducing catheter that is placed within the vasculature and is directed to the vessel or area where the misplaced or malfunctioning device is located. The snare can then capture the intended device and retrieve it out of the body through the introducing catheter or by withdrawing both the snare and the introducing catheter in tandem.

Currently available snares are designed using large diameter outer sheaths that require larger entry sites. This may result in complications such as excessive bleeding and/or hematomas. Additionally, because of the large diameter of the snare, it may be necessary to remove the existing catheters and exchange to larger introducing devices, which increases the overall time and cost of the procedure. A third disadvantage of the prior snares is that the outer sheath is typically made of a plastic material that exhibits little or no torque control, which makes ensnaring the misplaced or malfunctioned device difficult. Lastly, the prior snares are stiff and typically have sharp distal leading edges, which may damage vessel walls when the device is advanced into small diameter vessels such as those in the coronary and cerebral vasculature.

SUMMARY OF THE INVENTION

Accordingly, it is an object of the present invention to provide a snare that uses a relatively small diameter outer sheath that requires only a small entry site. Another object of the present invention is to provide a small diameter snare that does not require the removal of an existing catheter or exchange to other larger devices. A third object of the present invention is to provide a small diameter snare that exhibits superior torque control, to simplify ensnaring a misplaced or malfunctioned device.

To achieve the foregoing and other objects an improved snare is provided, having a diameter of 0.39" or less, that is capable of fitting through existing balloon or guiding catheters. The body of the snare includes metal tubing, which allows for a very thin wall thickness while providing stiffness for torque control and pushability. Additionally, a radiopaque coil may be attached to a distal end of the snare, to provide both visibility and a soft atraumatic leading edge.

Alternatively, or in addition, the snare employs a "D" shaped snare wire or wires to form the snare loop. This allows the wires to have a maximum cross sectional area within the confines of the inner diameter of the tubing, and thus, provides greater strength to the snare loop.

The snare may be further constructed with proximal end that is shaped to allow an extension to be added to the snare and thus enable catheters to be exchanged directly over the snare.

BRIEF DESCRIPTION OF THE DRAWINGS

The invention description below refers to the accompanying drawings, of which:

FIGS. 7–10 are partial cut-away diagrams of the snare of FIG. 5 with various shapes of snare loop; and.

Although the following Detailed Description will proceed upon reference being made to specific embodiments and methods of use, it should be appreciated that many alternatives, variations, and modifications thereof are possible without departing from the present invention. Accordingly, it is intended that the present invention be viewed broadly as encompassing all such alternatives, variations, and modifications.

DETAILED DESCRIPTION OF AN ILLUSTRATIVE EMBODIMENT

Figure 1:
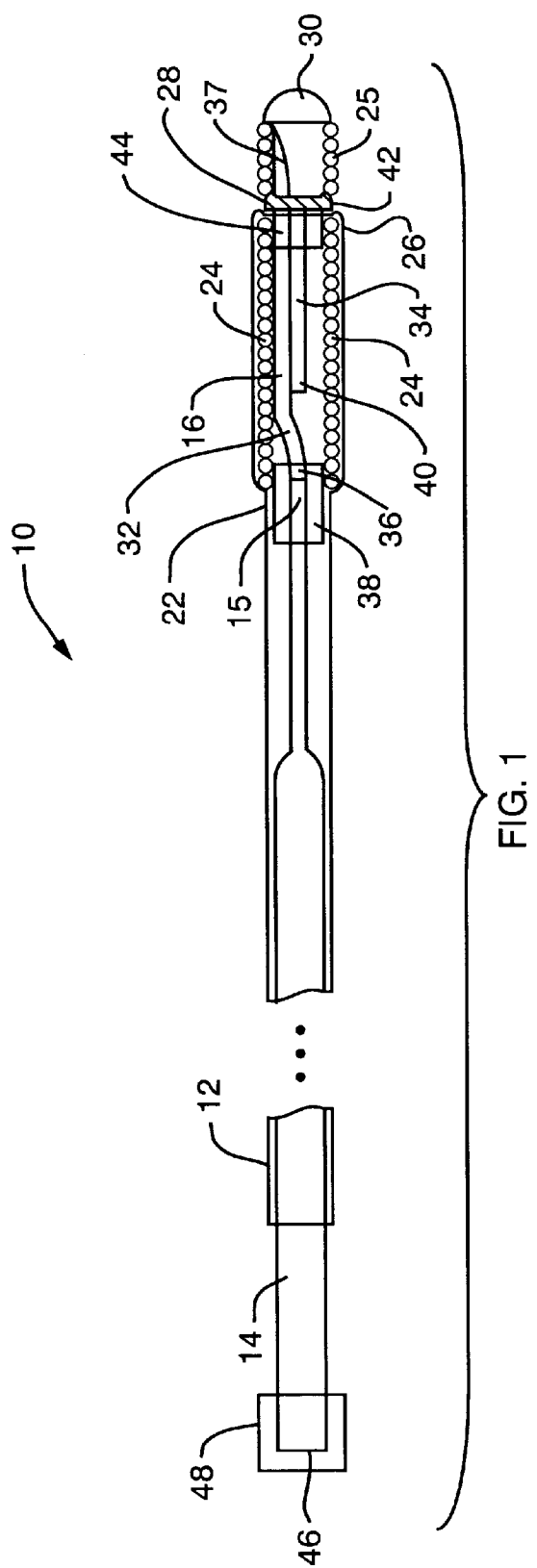
FIG. 1 is a highly schematic, cut-away diagram of one embodiment of a snare system according to the present invention.

Referring now to FIG. 1, a small diameter snare device 10 includes a hollow elongated stainless steel tube 12 through which a core wire 14 extends to support a snare loop 16. A distal end 22 of the tube supports a radiopaque coil 24, which provides visibility to the end of the tube under fluoroscopy. The coil also provides flexibility to the distal region of the device. A teflon shrink tube 26 fits over the coil and serves to prevent the coil from stretching when the snare loop is extended, as discussed below. As depicted in the drawing, a second radiopaque coil 25 may be attached to a distal end 28 of the snare loop 16, to provide visibility to the end of the loop under fluoroscopy. Further, an atraumatic tip 30 may be attached.

The snare loop 16 is formed from first and second snare wires 32 and 34, which are shaped to spring into a loop when the wires are pushed out of a distal end of the tube 12 and/or coil 24, as discussed below. The diameter of the snare wires is approximately 50% the diameter of the mid-section of the core wire, such that the snare device has an essentially uniform cross-section over its length. The snare wires may each have a D-shaped cross-section, to maximize the cross-sectional area and still fit within the inner diameter of the tube, as discussed in more detail below.

The wire 32 attaches at a proximal end 36 to a distal end 15 of the core wire 14, by brazing, soldering or other attachment mechanisms. A collar 38 supports the joint between the core and the first snare wire. A distal end 37 of the first wire supports the distal radiopaque coil 25 and the tip 30. As depicted in the drawing, the core wire may taper at the distal end, to accommodate the collar 38 and also to provide flexibility to the distal end of the device 10. Similarly, the distal end of the first snare wire may be tapered to provide greater flexibility.

The second snare wire 34 attaches to the first snare wire 32 at a proximal end 40 and a distal end 42 by brazing, soldering or the like. As shown, a collar 44 may support the joint at the distal end of the second wire.

A proximal end 46 of the core wire 14 supports a handle 48. The handle is used to control the positioning and orientation of the snare loop 16. When the handle is in a first position, as shown in the drawing, as the snare device is introduced into the body through a catheter 90 (FIG. 5). The snare loop 16 is thus pulled back inside the tube 12 and/or the coil 24. When the snare device is in place in the body, with the distal end of the device end adjacent to an object (not shown) that is to be removed from the body, the user pushes the handle in the direction of the distal end, to push the snare loop out of the end of the tube and/or coil. The snare wires 32 and 34 then spread into a shape for en-snaring the desired object. The snare wires may spread to shapes similar to those shown in FIGS. 2–11.

Once the snare loop 16 has ensnared the desired object, the user may pull on the handle 48, to draw the snare loop 16 slightly back into the tube 12 and/or coil 24 until the loop tightens around the object. The snare device 10 and, as appropriate, an introducing catheter, are then withdrawn from the body, to withdraw the ensnared object.

Figure 2:
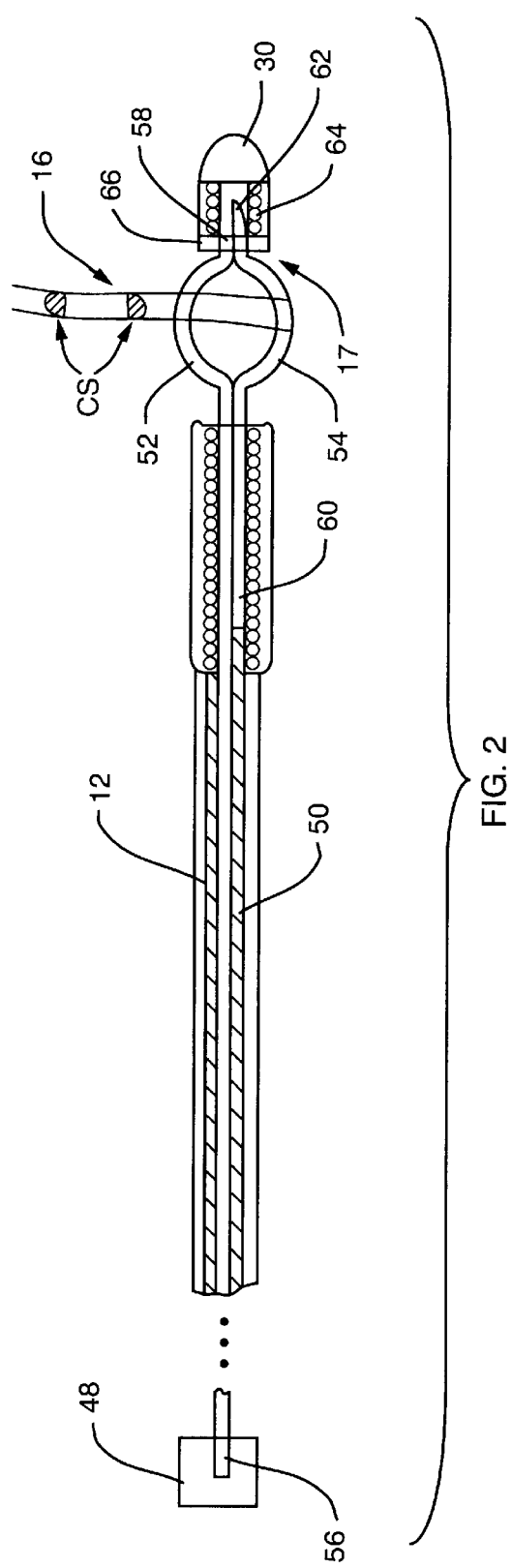
FIG. 2 is a highly schematic, cut-away diagram of another embodiment of a snare system according to the present invention.

Referring now to FIG. 2, the device may include a second stainless steel tube 50 that fits inside the tube 12. In this embodiment, a first snare wire 52 extends through the inner tube and the handle 48 (FIG. 1) attaches to a proximal end 56 of the first snare wire. The second snare wire 54 extends along a portion of the first snare wire and attaches at a proximal end 60 to the first snare wire by brazing, welding, soldering or the like. The distal end 58 of the first snare wire similarly attaches to the second snare wire. The distal end 62 of the second snare wire extends beyond the distal end of the first snare wire and supports a relatively short radiopaque coil 64 and the atraumatic tip 30. The coil 64 is approximately 1 mm in length. As shown, a collar 66 may support the joint at the distal end 17 of the loop 16.

Figure 3:
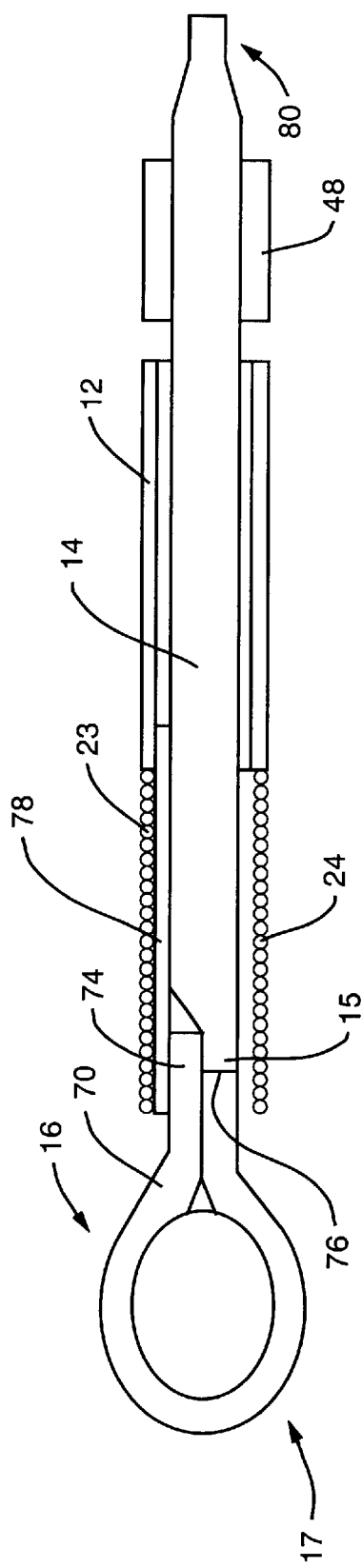
FIG. 3 is a highly schematic, cut-away diagram of a third embodiment of a snare system according to the present invention.
Figure 4:
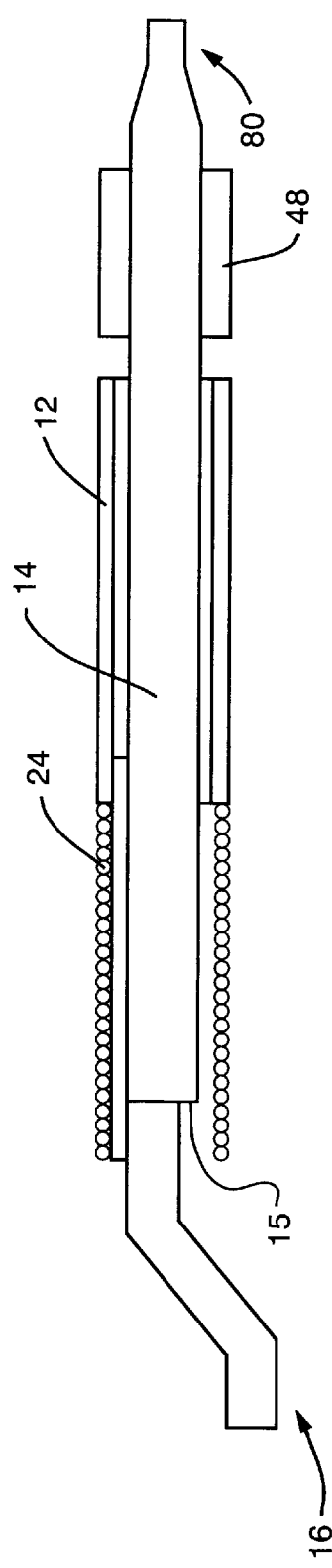
FIG. 4 illustrates a particular embodiment of the snare of FIG. 3.
Figure 5:
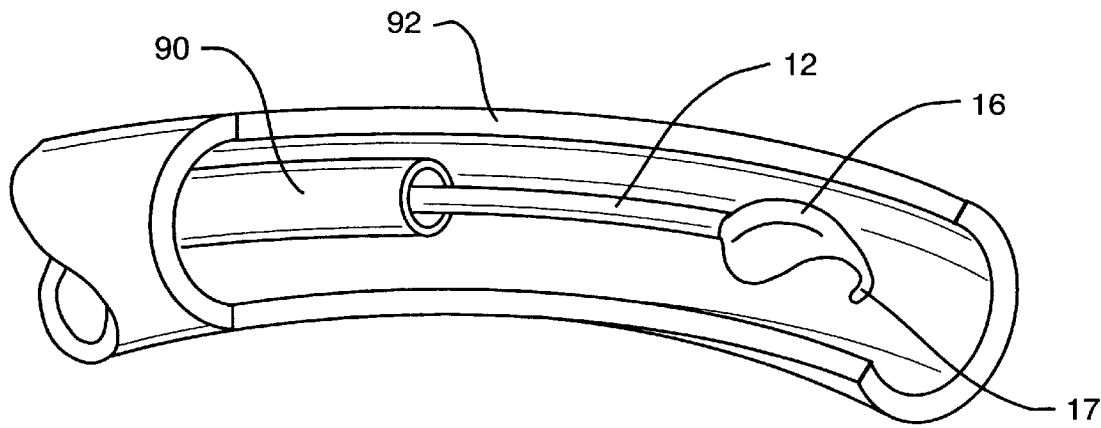
FIG. 5 is a diagram of a fifth embodiment of a snare system according to the present invention deployed in a catheter within an artery.

Referring now to FIGS. 3 and 4, the snare loop 16 may be formed from one or more shaped snare wires 70 that attach at proximal ends 74 and 76 to a tapered end distal end 15 of the core wire 14. A ribbon wire 78 extends from the proximal end 22 of the tube 12 to a proximal end 23 of the coil 24, and the coil and snare wires attach also to the ribbon wire. The distal end 17 of the loop 16 may be pinched a shown in FIG. 11, to support the second radiopaque coil 25 and the atraumatic tip 30 (FIG. 2). FIG. 4 depicts the loop 16 shaped to extend at an angle relative to the core wire 14. The proximal end 80 of the core wire 14 is shaped to allow extensions (not shown) to be fit onto the end of the snare device.

Figure 6:
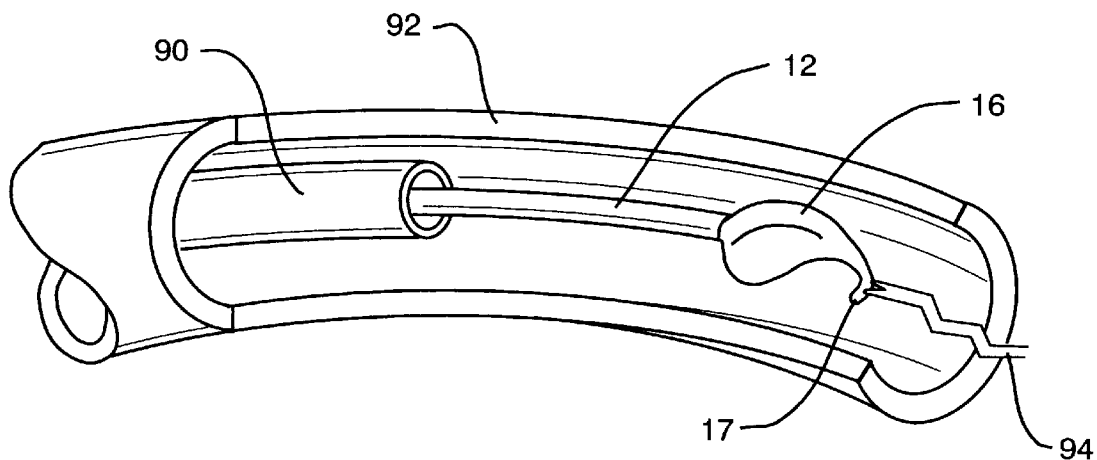
FIG. 6 is a diagram of the snare of FIG. 5 with a magnetic tip.
Figure 7:
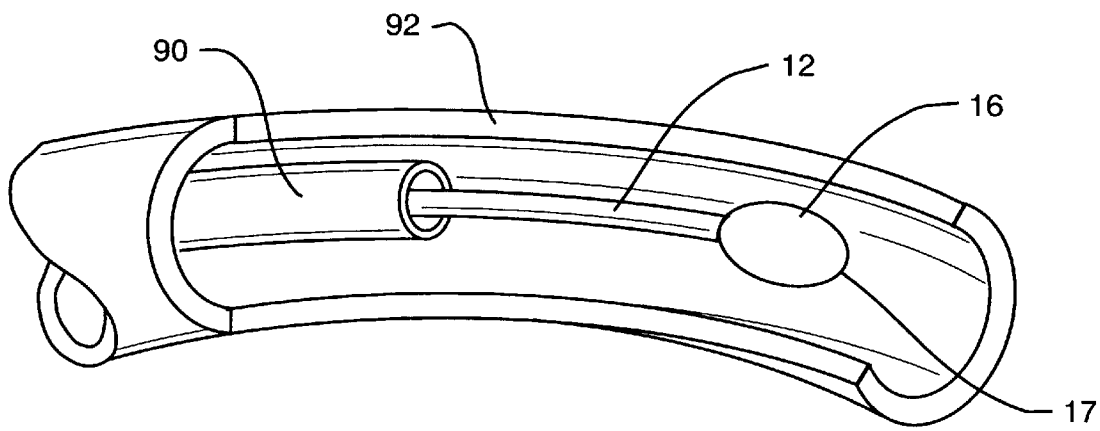
Figure 8:
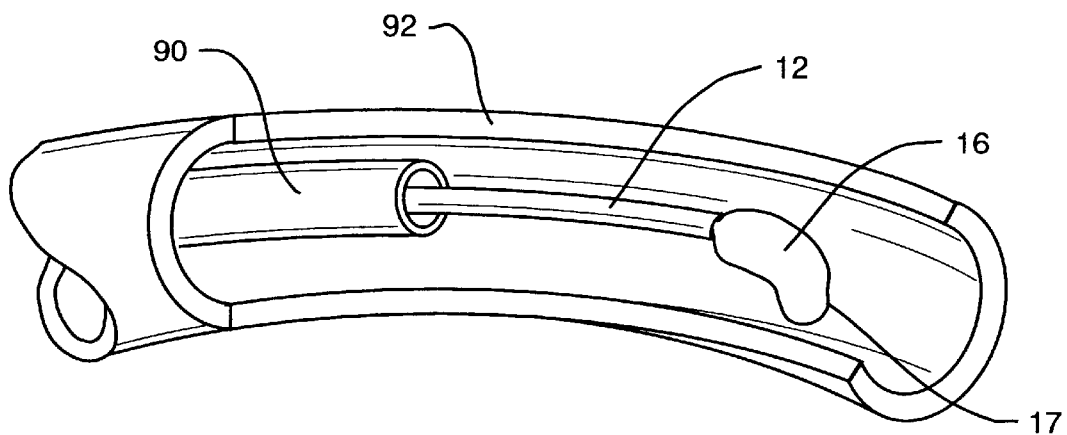
Figure 9:
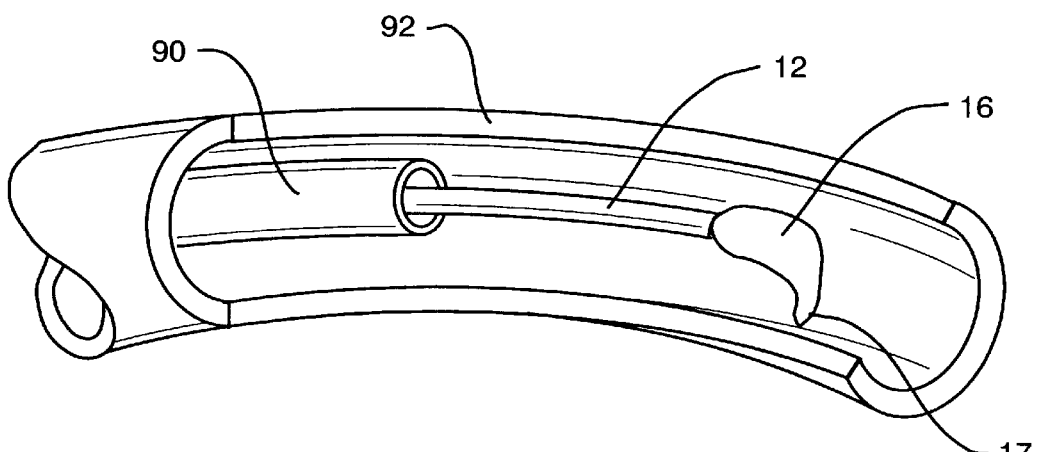
Figure 10:
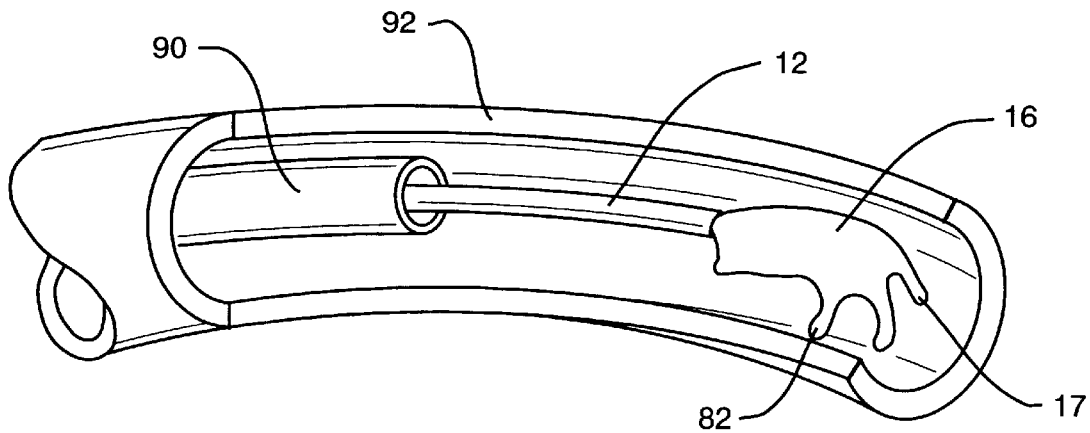

FIG. 5 depicts the snare device 10 in place in a catheter 90 that is introduced into an artery 92. As shown, the snare device may have a spiral shaped loop 16 that expands essentially to the full diameter of the artery. FIG. 6 depicts the device of FIG. 5 with a magnetic tip 94 attached to the distal end of the loop. The magnetic tip, which is included to attract metal objects (not shown) into the loop, may be various shapes. FIGS. 7–10 depict the snare device 10 with various shaped loops 16, with FIG. 10 showing the loop including multiple planar bends or fingers 82. The distal ends 17 of the various shaped loops 16 of FIGS. 5–10 may be pinched, as discussed above, to support the second radiopaque coil 25 and tip 30 (FIG. 2).

Figure 11:
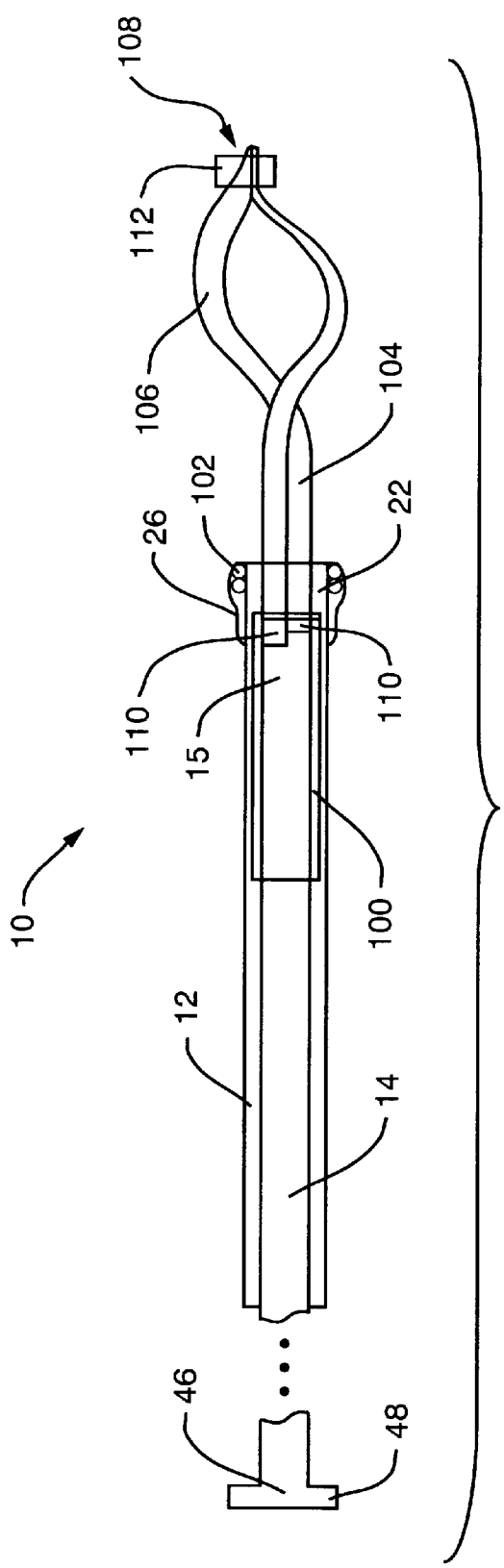
FIGS. 11 and 12 are highly schematic, cut away diagrams of a sixth embodiment of a snare system according to the present invention.
Figure 12:
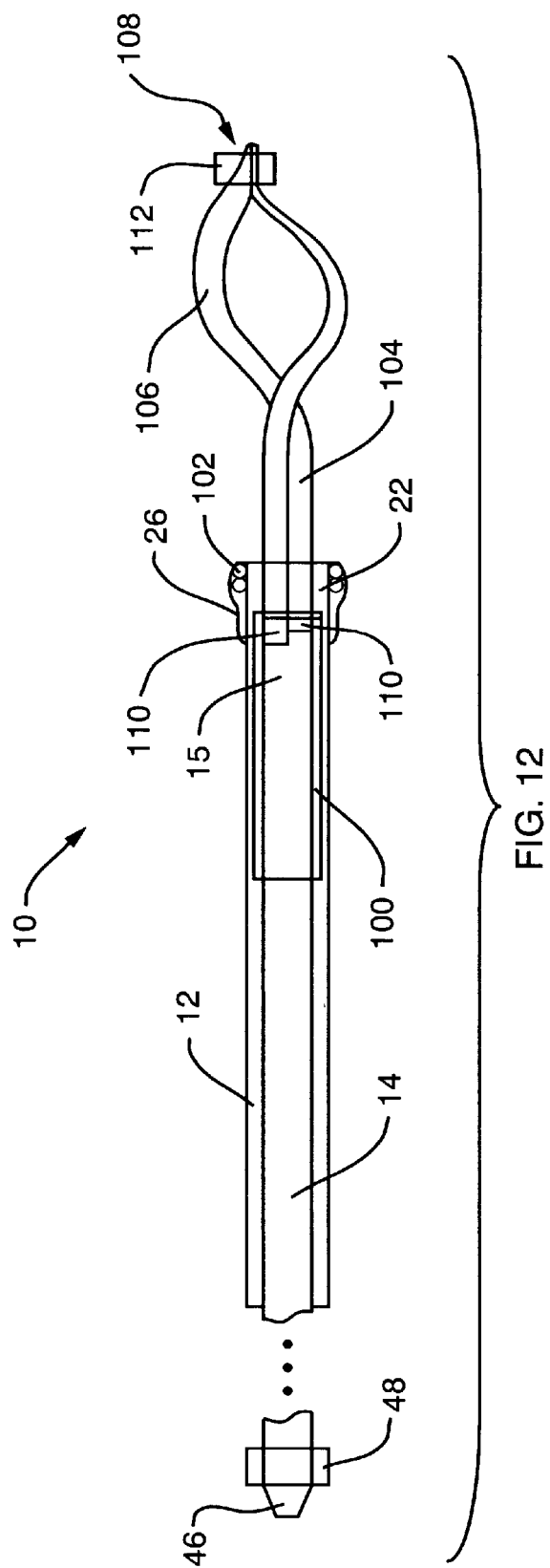

FIG. 11 depicts the snare device 10 with a thin-walled polyimide tube 100 fit into the distal end 22 of the metal tube 12. The polyimide tube, which has a high burst strength and is relatively stiff, provides torque control to the end of the device. A radiopaque marker 102 is positioned at the distal end of the polyimide tube and the shrink tube 26 is positioned over the marker and shrunk to hold the marker in place. The marker may be a 1 cm long radiopaque coil with a 0.020" outer diameter that is wound with 0.004"×0.012" wire. The snare loop 16, which is spiral shaped, is formed from two snare wires 104 and 106 that attach to one another at their distal ends 108 and to one another and to the core wire 14 at their proximal ends 110. A radiopaque collar 112 supports the joint at the distal ends of the wires and provides visibility. The collar may also support the is atraumatic tip 30 (FIG. 1). As depicted in the drawing, the proximal end 46 of the core wire 14 supports the handle 48. FIG. 12 depicts the device of FIG. 11 with a proximal end 114 that is shaped to allow an extension to slideably connect to the device.

In all embodiments, coatings can be applied to the core wire and/or to the outer surfaces of the tubing, to reduce friction between the core and the tube as well as to enhance movement of the snare device within a catheter.

The entire device when complete can be made less than 0.014" in diameter and is capable of being placed directly through a PTCA balloon catheter or other small diameter catheter that may already be in place within the patient. Alternatively, the snare may be passed through the guiding catheter along side of the balloon or access catheter without the need to remove the prior device and thus lose temporary access to the site within the patient.

As discussed previously, the snare wire or wires may have a half round or "D" shaped profile, to maximize the cross sectional area of the wire and thereby increase its overall breaking strength (see, for example, cross section CS in FIG. 2). For example, a tube with a 0.008" inner diameter can accommodate two 0.004" diameter round wires stacked together or the equivalent of a single 0.008" diameter wire if two "D" shaped wires are stacked. The total cross sectional area of a 0.004" diameter wire is 0.000013 sq. in. whereas the "D" shaped wire has a cross sectional area of a 0.000025 sq. in. Using the D-shape wire thus results in a doubling of the cross-sectional area and a likewise doubling of the breaking strength of the wire.

As also discussed, the proximal end of the core wire 14 and actuating handle 48 may be shaped such that an additional length or wire can be attached to the device, thereby extending the overall length of the device. This, in turn, allows one catheter to be exchanged for another catheter over the body of the snare. For example, the snare may be initially passed through a PTCA balloon catheter, which is already located within the target area. The balloon catheter can then be removed and replaced with a catheter that has a larger inner diameter, that may allow the snare and the ensnared object to be removed through the catheter.

Any combination of the tubing, central core, or snaring loop may be fabricated from a superelastic alloy such as Nitinol, to enhance the torquability or kink resistance of the device. Additionally, the snaring loop can be made as an integral part of the central core by reducing the diameter of the end of the central core and doubling this end over to form the loop. The terminal end of the core can then be attached to a more proximal section of the reduced-diameter core at a location at the base of the formed loop. As discussed, the distal end of the loop formed in the core wire may be pinched to form the distal end 17 that supports a radiopaque collar or other shaped marker.

Dimensional ranges contemplated for the above embodiments of the present invention include lengths of between 20 cm and 500 cm, diameters between 0.010" to 0.039" and loop diameters between 1 mm and 20 mm.

What is claimed is:

1. A surgical snare device for ensnaring objects in the vascular system, the snare including:
    A. a core wire with a proximal end and a distal end;
    B. tubing that extends over the core wire, the tubing including a metal section, the tubing having an outer diameter sized and arranged to allow the tubing to fit through a guiding or balloon catheter that is inserted into a blood vessel;
    C. a loop with a distal end and a proximal end, the loop including two snare wires that each attach at a respective distal end to one another and that each attach at a respective proximal end to the core wire;
    D. a first radiopaque marker that attaches to the distal end of the loop; and
    E. a handle that attaches to the proximal end of the core wire, the handle being pushed in the direction of the distal end of the device to push the loop out of a distal end of the tubing and being pulled in the opposite direction to pull all or a portion of the loop into the distal end of the tubing, and
    wherein each of the snare wires is constructed and arranged to spring away from one another to define the loop when each of the snare wires are pushed out of the distal end of the tubing and the snare wires are constructed and arranged to move toward each other as the snare wires are moved into the distal end of the tubing.

2. The snare device of claim 1 wherein the metal section of the tubing extends the length of the tubing and the tubing further includes a thin-walled inner tube that is positioned inside the distal end of the metal section.

3. The snare device of claim 2 wherein the inner tube is made of polyimide.

4. The snare device of claim 1 wherein the loop is spiral shaped.

5. The snare device of claim 1 wherein the first radiopaque marker is a collar that supports the joining of the distal ends of the snare wires.

6. The snare device of claim 5 further including a second radiopaque marker at the distal end of the tubing.

7. The snare device of claim 6 wherein the second radiopaque marker is a coil.

8. The snare device of claim 7 wherein the tubing includes a shrink tube that fits over the second radiopaque marker.

9. The snare device of claim 8 wherein the loop is spiral shaped.

10. The snare device of claim 1 wherein the loop is oval shaped.

11. The snare device of claim 1 wherein the loop is shaped with a plurality of planar bends.

12. The snare device of claim 1 wherein the loop includes a magnetic distal end.

13. The snare device of claim 1 wherein the loop is at an angle relative to the core wire when the loop is extended beyond the distal end of the tubing.

14. The snare device as set forth in claim 1 wherein each of the snare wires includes a half-round or D-shaped cross section and are stacked with respect to one another to form a predetermined-diameter round cross section.

15. The snare device of claim 1 wherein outer diameter of the tubing is 0.38 inch or less.

16. The snare device of claim 1 wherein the snare wires are constructed of a superelastic alloy.

17. A surgical snare device for ensnaring objects in the vascular system, the snare including:
    A. a core wire with a proximal end and a distal end;
    B. tubing that extends over the core wire, the tubing including a metal outer section and a polymer inner section, the inner section being positioned at a distal end of the tubing, and the tubing having an outer diameter sized and arranged to allow the tubing to fit through a guiding or balloon catheter that is inserted into a blood vessel;
    C. a loop with a distal end and a proximal end, the loop including two snare wires that each attach at a respective distal end to one another and that each attach at a respective proximal end to the core wire;
    D. a radiopaque marker that attaches to the distal end of the loop; and
    E. a handle that attaches to the proximal end of the core wire, the handle being pushed in the direction of the distal end of the device to push the loop out of a distal end of the tubing and being pulled in an opposite direction to pull all or a portion of the loop into the distal end of the tubing, and
    wherein each of the snare wires is constructed and arranged to spring away from one another to define the loop when each of the snare wires are pushed out of the distal end of the tubing and the snare wires are constructed and arranged to move toward each other as the snare wires are moved into the distal end of the tubing.

18. The snare device of claim 17 further including at the distal end of the tubing a radiopaque marker.

19. The snare device of claim 18 wherein the marker is a coil.

20. The snare device of claim 19 wherein the tubing includes a shrink tube that fits over the marker.

21. The snare device of claim 20 wherein the loop is spiral shaped.

22. The snare device of claim 17 wherein the loop is spiral shaped.

23. The snare device of claim 17 wherein the loop is oval shaped.

24. The snare device of claim 17 wherein the loop is shaped with a plurality of planar bends.

25. The snare device of claim 17 wherein the loop includes a magnetic distal end.

26. The snare device of claim 17 wherein the loop is at an angle relative to the core wire when the loop is extended beyond the distal end of the tubing.

27. The snare device of claim 17 wherein each of the snare wires includes a half-round or D-shaped cross section and are stacked with respect to one another to form a predetermined-diameter round cross section.

28. The snare device of claim 17 wherein outer diameter of the tubing is 0.38 inch or less.

29. The snare device of claim 17 wherein the snare wires are constructed of a superelastic alloy.

30. The snare device of claim 17 wherein the polymer inner section comprises a polyimide inner section.

* * * * *